(12) United States Patent
Hauk

(10) Patent No.: US 8,323,795 B2
(45) Date of Patent: Dec. 4, 2012

(54) EASY-TO-SUSPEND HYDROPHOBING AGENTS

(75) Inventor: Juergen Hauk, Freising (DE)

(73) Assignee: Baerlocher GmbH (DE)

( * ) Notice: Subject to any disclaimer, the term of this patent is extended or adjusted under 35 U.S.C. 154(b) by 105 days.

(21) Appl. No.: 12/810,558

(22) PCT Filed: Dec. 15, 2008

(86) PCT No.: PCT/EP2008/010655
§ 371 (c)(1),
(2), (4) Date: Sep. 14, 2010

(87) PCT Pub. No.: WO2009/083127
PCT Pub. Date: Jul. 9, 2009

(65) Prior Publication Data
US 2011/0014471 A1   Jan. 20, 2011

(30) Foreign Application Priority Data
Dec. 27, 2007   (DE) .......... 10 2007 062 774

(51) Int. Cl.
*A61K 8/11* (2006.01)
*B01J 2/30* (2006.01)
(52) U.S. Cl. .................. 428/403; 427/213.31; 264/4.32
(58) Field of Classification Search ..... 428/402–402.24; 427/213.3–213.36; 264/4–4.7
See application file for complete search history.

(56) References Cited

U.S. PATENT DOCUMENTS

| 3,461,081 A | 8/1969 | Matsuo |
|---|---|---|
| 4,168,241 A | 9/1979 | Kozima |
| 4,247,338 A | 1/1981 | Ziobrowski |
| 4,590,142 A * | 5/1986 | Yamazaki et al. ............ 430/138 |
| 5,352,441 A | 10/1994 | Mausner |
| 5,624,747 A * | 4/1997 | Sarkar et al. ............... 428/32.14 |
| 2006/0051696 A1* | 3/2006 | Tsutsui et al. ............... 430/125 |
| 2006/0167138 A1 | 7/2006 | Ishii et al. |
| 2006/0254468 A1 | 11/2006 | Bastelberger |

FOREIGN PATENT DOCUMENTS

| EP | 0 330 889 | 9/1989 |
|---|---|---|
| EP | 1547987 | 6/2005 |
| GB | 1267482 | 3/1972 |
| WO | 9006974 | 6/1990 |
| WO | 2004/036187 | 4/2004 |
| WO | 2004/103928 | 12/2004 |

OTHER PUBLICATIONS

International Search Report, mailed Mar. 31, 2009, in corresponding International Application No. PCT/EP2008/010655, 4 pages.
International Preliminary Report on Patentability, mailed Aug. 19, 2010 in related International Application No. PCT/EP2008/010655, 6 pages.

* cited by examiner

*Primary Examiner* — Nathan M Nutter
(74) *Attorney, Agent, or Firm* — McKeon, Meunier, Carlin & Curfman, LLC

(57) ABSTRACT

The invention relates to solids powders comprising particles having an average particle size of 0.1 to 50 µm with predominantly a core-shell structure, wherein the core comprises at least one water-insoluble fatty acid salt and the shell at least one anionic, cationic or non-ionic emulsifier, and the solids powder when introduced into water or at least one polar organic solvent or a mixture comprising water and at least one polar organic solvent, at a temperature of 23° C. while exposed to a mechanical force, forms a complete dispersion within 60 minutes or less.

12 Claims, No Drawings

EASY-TO-SUSPEND HYDROPHOBING AGENTS

FIELD

The present invention relates to a solids powder comprising particles having an average particle size of from 0.1 to 50 µm with predominantly a core-shell structure, wherein the core comprises at least one water-insoluble fatty acid salt and the shell at least one anionic, cationic or nonionic emulsifier, and the solids powder when introduced into water or at least one polar organic solvent or a mixture comprising water and at least one polar organic solvent, at a temperature of 23° C. while exposed to a mechanical force, forms a complete dispersion within 60 minutes or less.

BACKGROUND

The use of fatty acid compounds for hydrophobing surfaces has already been known for a long time. For this purpose, the corresponding fatty acid compounds are as a rule converted into an aqueous dispersion while exposed to high shearing forces, optionally with the addition of an emulsifier or an emulsifier mixture. This dispersion is then further processed appropriately, in order to achieve hydrophobing of the desired surface.

However, problems arise in the procedure carried out to date, in that the materials employed for the hydrophobing are exceptionally difficult to convert into aqueous dispersions because of their hydrophobic properties. In particular, when fatty acid salts are employed as hydrophobing agents, the phenomenon of the fatty acid compounds floating on the surface of water and being able to be converted into a complete dispersion only under a high mechanical effort often arises. This behavior leads both to an increased consumption of time and to higher costs for the user.

SUMMARY

The present invention was therefore based on the object of providing a solids powder which is suitable for hydrophobing and does not have the disadvantages occurring in practice to date. In particular, the present invention was based on the object of providing a solids powder which is suitable for hydrophobing surfaces and can be converted into a complete dispersion by the user in a short time and with the lowest possible mechanical effort.

It has now been found that in particular solids particles having a core-shell structure achieve the abovementioned object if the core comprises at least one water-insoluble fatty acid salt and the shell at least one anionic, cationic or nonionic emulsifier.

The present invention therefore relates to a solids powder comprising particles having an average particle size of from 0.1 to 50 µm with predominantly a core-shell structure, wherein the core comprises at least one water-insoluble fatty acid salt and the shell at least one anionic, cationic or nonionic emulsifier, and the solids powder when introduced into water or at least one polar organic solvent or a mixture comprising water and at least one polar organic solvent, at a temperature of 23° C. while exposed to a mechanical force, forms a complete dispersion within 60 minutes or less.

The solids powder according to the invention is distinguished in that when introduced into water or at least one polar organic solvent or a mixture comprising water and at least one polar organic solvent, while exposed to a mechanical force, it is dispersible. In the context of the present invention, an "introduction into water or at least one polar organic solvent or a mixture comprising water and at least one polar organic solvent" is understood as meaning the introduction into a composition which comprises at least a proportion of water or at least one polar organic solvent or a mixture comprising water and at least one polar organic solvent. In the context of the present invention, the abovementioned introduction into water or at least one polar organic solvent or a mixture comprising water or at least one polar organic solvent is thus to be understood as meaning, for example, the introduction into water or a polar organic solvent or a mixture of two or more polar organic solvents or a mixture comprising water or at least one polar organic solvent, wherein the particular constituents in total can make up essentially 100% of the substance mixture into which the introduction takes place. However, it is equally envisaged according to the invention that the introduction takes place into a composition which takes place water or at least one polar organic solvent or a mixture comprising water and at least one polar organic solvent only to a content, based on the total mixture, making up less than 100 by weight, for example to a content of 80, 60, 40, 20 or about only 10 by weight.

In this context, the content lacking, to make up 100% by weight, can contain, for example, oligomeric or polymeric constituents or other auxiliary substances, fillers and the like, such as are contained, for example, in coating compositions, such as emulsion paints or water-based lacquers.

DETAILED DESCRIPTION

In the context of the present text, "exposure to a mechanical force" is understood as meaning a measure which results in a movement of the mixture of water and solids powder which is preferably sufficient to form a complete dispersion within 60 minutes. Suitable forms of exposure to a mechanical force are, for example, stirring with suitable stirring devices, Ultraturrax, a dissolver disk or other methods, such as ultrasound.

In the context of the present invention, a "complete dispersion" is understood as meaning a state in which the solids powder is present in water in an essentially completely wetted form and no non-wetted particles settle on the surface of the water even after a standing time of at least one minute, preferably at least 5 minutes or at least 1 hour.

In the context of the present invention, a core-shell structure is understood as meaning a structure in which the composition of the solid particle changes, starting from the central point of the particle towards the edges, such that the edge has a different composition to the middle. In the context of the present invention, such changes can be continuous or essentially discontinuous or a mixture of the two phenomena. In the context of the present invention, a "predominantly core-shell structure" is understood as meaning the finding that the core-shell structure can be detected for at least about 40% of the surface of the solid particle. Appropriate detection methods are known to the person skilled in the art, for example analysis of the solid particles can be carried out by electron microscopy.

In the context of the present invention, a solids powder according to the invention comprises particles having an average particle size of from about 0.1 to about 50 µm, for example about 0.5 to about 30 or about 1 to about 20 µm. Suitable methods for determination of the particle size are known to the person skilled in the art, and laser diffractometry may be mentioned here in particular.

The individual particles of a solids powder according to the invention comprise a core which is made of a core material which comprises at least one water-insoluble fatty acid salt.

In this context, the core itself can be made of an appropriate water-insoluble fatty acid salt or comprise a mixture of 2 or more fatty acid salts, at least one of which must be water-insoluble, or a mixture of a water-insoluble fatty acid salt and one or more further compounds. However, in the context of the present invention it is likewise possible for the core itself already to have a core-shell structure. It is thus envisaged according to the invention, for example, that a structure which in its turn has as a core an inorganic or organic carrier, for example a filler, such as chalk or titanium dioxide, which has on its surface an appropriate water-insoluble fatty acid salt is employed as the core. Such structures have the advantage that in many cases they require a significantly reduced content of expensive fatty acid salts for an identical effectiveness with respect to the hydrophobing action, and are therefore significantly more economically favorable. Such core structures are employed in particular in systems in which the exposure to heat does not exceed the melting point of the fatty acid salts employed or of the fatty acid salt.

It has moreover also proved appropriate for the core to comprise an inorganic or organic carrier material which has a porous structure which is, for example, absorbent for one or more further constituents of the core material. Suitable materials are e.g. zeolites or laminar compounds, such as hydrotalcites and the like.

In the context of a further embodiment of the present invention, the core material of a solids powder according to the invention therefore comprises at least one organic or inorganic carrier material.

In the context of the present invention, suitable fatty acid salts are the salts of the aliphatic carboxylic acids of the formula (I)

$$R^1CO\text{—}OH \qquad (I)$$

in which $R^1CO$ represents an aliphatic, linear or branched acyl radical having 6 to 22 carbon atoms and 0 and/or 1, 2 or 3 double bonds.

Typical examples of suitable fatty acids are caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical grade mixtures thereof which are obtained e.g. during pressure cracking of natural fats and oils, during reduction of aldehydes from Roelen's oxo synthesis or dimerization of unsaturated fatty acids.

The salts of technical grade fatty acids having 12 to 18 carbon atoms, such as, for example, coconut, palm, palm kernel or tallow fatty acid are preferred.

In the context of a further embodiment, the core contains a fatty acid salt with a metal cation or an ammonium cation or a mixture of fatty acid salts of at least two different metal cations or two different ammonium cations or a mixture of at least one metal cation and at least one ammonium cation, wherein the metal cations are chosen from the group consisting of alkali metals, alkaline earth metals, zinc, aluminum and rare earths.

The salts of saturated and the salts of unsaturated fatty acids are suitable as a constituent of the core according to the invention. It may be preferable to employ the salts of saturated fatty acids, but in some cases it has also proved advantageous to employ the salts of unsaturated fatty acids.

Suitable metal cations for formation of the fatty acid salts are, in particular, metal cations chosen from the group of cations of alkali metals, alkaline earth metals, zinc, aluminum and rare earths.

Preferred alkali metal salts are the salts of lithium, sodium and potassium. Preferred alkaline earth metal salts are the salts of magnesium, calcium, strontium and barium. Among the salts of the rare earths, cerium and lanthanum are suitable in particular.

In a preferred embodiment of the invention, the fatty acid salts are at least one fatty acid salt from the group of alkali metal salts or at least one fatty acid salt from the group of alkaline earth metal salts or a fatty acid salt of at least one metal from the group of rare earths or a mixture of two or more thereof. It may be preferable for a core according to the invention to comprise at least one alkali metal salt or at least one alkaline earth metal salt or a mixture of the two. For example, fatty acid salt mixtures which comprise sodium, or potassium and calcium or magnesium salts of appropriately suitable fatty acids are suitable.

In a further preferred embodiment, for example, a mixture of sodium and calcium salts is employed. In a further preferred embodiment of the invention, a solids powder according to the invention can a mixture of about 10 to about 50 wt. % of sodium salts and about 90 to about 50 wt. % of calcium salts, based on the total weight of the fatty acid salts in the fatty acid salt mixture. The use of sodium and calcium salts in the weight ratio of about 1:2 is particularly preferred.

If a core material according to the invention comprises fatty acids of different chain lengths, it may be possible in principle for different metal cations to be present essentially in random distribution over the fatty acids with different chain lengths. If a core material according to the invention comprises saturated and unsaturated fatty acids, it may be possible in principle for different metal cations to be present essentially in random distribution over the saturated and the unsaturated fatty acids. In the context of the present invention, however, it is equally envisaged that different fatty acids which differ, for example, in chain length or in saturation have identical cations, for example identical metal cations, or different cations distributed in a statistically significant manner.

In a particular embodiment, fatty acid salts which are suitable for a core material which can be employed according to the invention are obtained, for example, when a fat or oil is reacted with a suitable metal compound or a mixture of two or more suitable metal compounds, for example metal oxides, metal hydroxides, metal carbonates or metal salts of mineral acids, for example sodium hydroxide or calcium hydroxide or both.

The amounts chosen for the metal salts are, for example, stoichiometric to the amounts of the desired salts. In a particular embodiment of the invention, the direct process product of such a reaction can be employed as the core material. In this case, no further purification steps are required after the hydrolysis step.

In the context of the present invention, suitable cations in core materials which are suitable according to the invention are in principle all compounds which lead to an ammonium salt of the corresponding fatty acid by an appropriate reaction. In the context of the present text, in this context ammonia is also described as "amine". In this context, ammonium salts according to the invention can be obtained, for example, by appropriate reaction of amines or amides, such as alkylmonoamines, alkyldiamines, alkylpolyamines, dialkylamines or polyalkylamines. Suitable ammonium salts are therefore derived, for example, from primary mono- or polyamino compounds having 2 to about 40, for example 6 to about 20 C atoms. These are, for example, ammonia, methylamine, ethylamine, n-propylamine, i-propylamine, n-propylamine, sec-propylamine, tert-butylamine, the isomeric pentylamines, hexylamines, heptylamines and higher homologues thereof having 8, 9, 10, 11, 12, 13, 14, 15, 16, 17, 18, 19, 20, 21 or 22 C atoms, for example stearylamine, 1-aminoisobutane, substituted amines having 2 to about 20 C atoms, such as 2-(N,N-dimethylamino)-1-aminoethane. Suitable diamines are have, for example, a molecular weight of from about 32 to about 200 g/mol, the corresponding diamines containing, for example, two primary, two secondary or one primary and one secondary amino group. Examples of these are diaminoethane, the isomeric diaminopropanes, the isomeric diaminobutanes, the isomeric diaminohexanes, pipearzine, 2,5-dimethyl-piperazine, amino-3-aminomethyl-3,5,5-trimethylcyclo-hexane (isophoronediamine, IPDA), 4,4'-diamino-dicyclohexyl-methane, 1,4-diaminocyclohexane, amino-ethylethanolamine, hydrazine, hydrazine hydrate or triamines, such as diethylenetriamine or 1,8-diamino-4-aminomethyloctane. Triethylamine, tributylamine, dimethylbenzylamine, N-ethyl-, N-methyl-, N-cyclohexyl-morpholine, dimethylcyclohexylamine, dimorpholino-diethyl ether, 1,4-diazabicyclo[2,2,2]octane, 1-azabicyclo[3,3,0] octane, N,N,N',N'-tetramethyl-ethylenediamine, N,N,N',N'-tetramethylbutanediamine, N,N,N',N'-tetramethylhexane-1,6-diamine, pentamethyl-diethylenetriamine, tetramethyl-diaminoethyl ether, bis-(dimethylaminopropyl)-urea, N,N'-dimethyl-piperazine, 1,2-dimethylimidazole or di-(4-N,N-dimethylaminocyclohexyl)-methane.

Aliphatic amino alcohols having 2 to about 40, preferably 6 to about 20 C atoms, for example triethanolamine, tripropanolamine, tributanolamine, tripentanolamine, 1-amino-3,3-dimethylpentan-5-ol, 2-aminohexane-2',2"-diethanolamine, 1-amino-2,5-dimethylcyclohexan-4-ol, 2-aminopropanol, 2-aminobutanol, 3-aminopropanol, 1-amino-2-propanol, 2-amino-2-methyl-1-propanol, 5-aminopentanol, 3-aminomethyl-3,5,5-trimethylcyclohexanol, 1-amino-1-cyclopentanemethanol, 2-amino-2-ethyl-1,3-propanediol, 2-(dimethylaminoethoxy)-ethanol, aromatic-aliphatic or aromatic-cycloaliphatic amino alcohols having 6 to about 20 C atoms, wherein heterocyclic or isocyclic ring systems as aromatic structures, such as naphthalene derivatives or in particular benzene derivatives, such as 2-aminobenzyl alcohol, 3-(hydroxymethyl)aniline, 2-amino-3-phenyl-1-propanol, 2-amino-1-phenylethanol, 2-phenylglycinol or 2-amino-1-phenyl-1,3-propanediol and mixtures of two or more such compounds are likewise suitable. Compounds which are likewise suitable as ammonium salts are, for example, those in which the amino group is present bonded to a substituted aromatic or heteroaromatic system, for example aminobenzoic acid, aminosalicylic acid or aminopyridinecarboxylic acid and suitable derivatives thereof.

In the context of the present invention, core materials which are employed are furthermore substances which in turn can themselves serve as a carrier material for a fatty acid compound having a hydrophobing action, in particular a fatty acid salt having a hydrophobing action. Suitable carrier materials are, for example, inorganic carriers, such as chalk or titanium dioxide, inorganic porous carriers, such as montmorillonite, bleaching earth and the like, organic carriers, such as starch, microcellulose and similar, and zeolites or hollow microbodies or mixtures of two or more thereof.

In the context of the present invention, it is moreover envisaged that the core material comprises, based on the the total weight of the fatty acid salts in the core material, at least 1 wt. %, for example 5 wt. % or more or 10 wt. % or more or 15 wt. % or more or 20 wt. % or more or 25 wt. % or more or 30 wt. % or more or 35 wt. % or more or 40 wt. % or more or 45 wt. % or more, or 50 wt. % or more or 55 wt. % or more or 60 wt. % or more of 65 wt. % or more or 70 wt. % or more or 75 wt. % or more or 80 wt. % or more or 85 wt. % or more of fatty acid salts which have a water-solubility at room temperature of less than 1 g/l, preferably less than 0.1 g/l. For example, a core material which can be employed in the context of the invention comprises fatty acids having a chain length of from about 12 to about 24 C atoms. In this context, it has proved to be advantageous when, if the core material comprises fatty acids having a chain length of 16 C atoms or less, these fatty acids are present in the form of their alkaline earth metal salts or as salts of the rare earths to the effect that their water-solubility is below the abovementioned maximum values.

A solid particle which can be employed in the context of the present invention also comprises, in addition to a core according to the abovementioned definition, a shell. In this context, the shell contains at least one anionic, cationic or nonionic emulsifier which displays an action to the effect that the solids powder when introduced into water or at least one polar organic solvent or a mixture comprising water and at least one polar organic solvent, at a temperature of 23° C. while exposed to a mechanical force, forms a complete dispersion within 60 minutes or less.

In the context of the present invention, suitable inorganic emulsifiers are in principle all emulsifiers which fulfill the aim set according to the invention with respect to the emulsifiability of the solids in water. In this context, for example, the salts of fatty acids, in particular the salts of fatty acids having a chain length of from 8 to 17 C atoms, are particularly suitable. This is particularly preferable in the context of the present invention if the content of such fatty acid salts in the shell, based on the total amount of the fatty acid salts in the shell, makes up 20 wt. % or more than 20 wt. %. In this context, the fatty acid salts present in the shell are preferably at least 70 wt. % alkali metal salts or amino salts, based on the total amount of fatty acid salts present in the shell.

Anionic emulsifiers which are furthermore suitable and can be employed as a constituent of the shell are alkylbenzenesulfonates, alkanesulfonates, olefin-sulfonates, alkyl ether-sulfonates, glycerol ether-sulfonates, α-methyl ester-sulfonates, sulfo-fatty acids, alkyl sulfates, fatty alcohol ether-sulfates, glycerol ether-sulfates, hydroxy-mixed ether-sulfates, monoglyceride (ether) sulfates, fatty acid amide (ether)sulfates, mono- and dialkyl sulfosuccinates, mono- and dialkyl sulfosuccinamates, sulfotriglycerides, amide soaps, ether-carboxylic acids and salts thereof, fatty acid isethionates, fatty acid sarcosinates, fatty acid taurides, acyl lactylates, acyl tartrates, acyl glutamates, acyl aspartates, alkyl oligoglucoside-sulfates, protein-fatty acid condensates (in particular plant products based on wheat) and alkyl (ether) phosphates. If the anionic surfactants contain polyglycol ether chains, these can have a conventional, but preferably a narrowed distribution of homologues.

A shell which can be employed according to the invention can moreover comprise nonionic surfactants, in addition to or instead of the anionic surfactants.

Typical examples of suitable nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, alk(en)yl oligoglycosides, fatty acid N-alkylglucamides, protein hydrolysates (in particular plant products based on wheat), polyol fatty acid esters, sugar esters, sorbitan esters, polysorbates and amine oxides. If the nonionic surfactants contain polyglycol ether chains, these can have a conventional, but preferably a narrowed distribution of homologues.

Cationic surfactants or zwitter-ionic surfactants are likewise suitable as constituents of the shell. Typical examples of cationic surfactants are quaternary ammonium compounds and ester-quats, in particular quaternized fatty acid trialkanolamine ester salts. Typical examples of amphoteric or zwitter-ionic surfactants are alkylbetaines, alkylamidobetaines, aminopropionates, aminoglycinates, imidazoliniumbetaines and sulfobetaines.

In a further embodiment of the invention, the content of fatty acid salts having 8 to 17 C atoms in the total fatty acid salts in the shell is more than 30, 50, 60, 70 or 80 wt. %.

In a preferred embodiment of the invention, a shell according to the invention comprises fatty acid salts chosen from the group consisting of fatty acid salts of caprylic, pelargonic, capric, lauric, lauroleic, myristic, myristoleic, palmitic, palmitoleic, margaric, undecylenic and palmitoleic acid. Further preferred fatty acids are linoleic acid and linolenic acid. Fatty acids which contain one or more OH groups or one or more epoxy groups, for example, are moreover suitable.

In a further embodiment of the invention, the sum of the contents of fatty acid salts of the caprylates, laurates and myristates in the total fatty acid salts present in the shell makes up more than 50% by weight. In addition to the constituents described above, a solids powder according to the invention can also comprise further constituents. These are, for example, polyfunctional alcohols. Compounds which contain at least 2 OH groups are called polyfunctional alcohols. Linear, branched, saturated or unsaturated and homocyclic or heterocyclic unsaturated alcohols are suitable in principle as a constituent of the solids powders according to the invention. In some cases however, it has proved advantageous if compounds which contain only carbon, hydrogen and oxygen as atomic constituents are employed as polyfunctional alcohols. The molecular weight of appropriate polyfunctional alcohols can be between about 62 (ethylene glycol) you several thousand, for example about 100,000. In this context, a solids powder according to the invention can comprise, for example, only one polyfunctional alcohol or two or more polyfunctional alcohols. The alcohols can differ, for example, in their molecular weight or in the number of OH groups or in several different features.

Suitable polyfunctional alcohols are, for example, those such as ethylene glycol, propylene glycol, butylene glycol, pentylene glycol, hexylene glycol, propanetriol, trimethylolpropane, pentaerythritol, dihydroxycyclohexane, diethylene glycol, triethylene glycol and the dimers, trimeric or oligomeric derivatives of the abovementioned dialcohols, oligoglycerol, polyglycerol, polyvinyl alcohol and the like.

It may be preferable according to the invention if a solids powder comprises a low molecular weight polyfunctional alcohol having 2, 3 or 4 OH groups, in particular propanetriol, in the shell.

The content of polyfunctional alcohol or polyfunctional alcohols is, if these compounds are contained in the solids powder according to the invention, up to about 40 wt. %, in particular about 1 to about 30 or about 5 to about 20 or about 8 to about 13 wt. %, preferably as a constituent of the shell.

A solids powder according to the invention can moreover comprise one or more monoalcohols, for example fatty alcohols. Linear or branched, saturated or unsaturated aliphatic monofunctional alcohols are suitable here, in particular methanol, ethanol, the isomers of propanol, butanol or hexanol and fatty alcohols having about 8 to about 22 C atoms, for example octanol, decanol, dodecanol, tetradecanol, hexadecanol or octadecanol are employed. The fatty alcohols mentioned are obtainable, for example, by reduction of natural fatty acids and can be employed both as pure substances and in the form of their technical grade mixtures. Linear monoalcohols, for example, are particularly suitable, and in particular those having about 4 to about 18 C atoms. Instead of the linear or branched aliphatic alcohols or in a mixture with these, monoalkyl polyether-alcohols of different molecular weight, preferably in the molecular weight ranges of from about 1,000 to about 2,000, can also be employed.

The solids powder according to the invention can be employed in principle for any desired purposes. However, in the context of the present invention it has been found that the solids powder is excellently suitable for imparting to surfaces certain properties with respect to their interaction with water or polar solids, in particular for rendering these materials hydrophobic. A solids powder according to the invention is therefore suitable as a hydrophobing agent. Where reference is made to hydrophobing agents in the context of the present text, this is to be understood as also meaning reference to the solids powders according to the invention.

In a further embodiment of the invention, the solids powder comprises additives. Suitable additives are contained, for example, solvents, binders, solubilizing agents, fillers, further hydrophobing agents, surfactants, emulsifiers, viscosity improvers, pigments, dyestuffs, preservatives, gelling agents, anticaking agents, pH modifiers, buffers, reaction accelerators, reaction retardants, colloids, polymers or air entraining agents or mixtures of two or more thereof.

A solids powder according to the invention can additionally comprise, for example, binders, surfactants, emulsifiers, colloids or polymers. These additives are present, for example, in order to improve the dispersibility and miscibility of the solids powder in a further material, in particular a building material. Appropriate additives which can be employed according to the invention are fatty acid derivatives, such as esters, waxes, polymers, in particular ionic polymers and detergents.

Binders which are employed are, for example, water-soluble or water-dispersible binders. Such substances are known in the literature. Preferably, substances which have a wax-like, highly viscous or solid consistency at room temperature, i.e. between 20 and 25° C., and have a melting point of from 25° C. to 150° C. are employed. Examples of conventional appropriate binding materials are polyvinyl alcohol, methylcellulose, carboxymethylcellulose, ethoxylated fatty alcohols or mixtures thereof. Fatty acid esters or film-forming polymers can moreover be employed. The binding materials should not interfere or should only interfere as little as possible with the hydrating process of the building material when water is introduced.

Preferred colloids are partly hydrolyzed and completely hydrolyzed polyvinyl alcohols, polyvinylpyrrolidones, polyvinyl acetals, polysaccharides in water-soluble form, such as starches (amylose and amylopectin), celluloses and carboxymethyl, methyl, hydroxyethyl, hydroxypropyl derivatives thereof, proteins, such as casein or caseinate, soya protein, gelatin, ligninsulfonates, synthetic polymers, such as poly(meth)acrylic acid, copolymers of (meth)acrylates with carboxyl-functional comonomer units, poly(meth)acrylamide, polyvinylsulfonic acids and water-soluble copolymers thereof; melamine-formaldehyde sulfonates, naphthalene-formaldehyde sulfonates, styrene/maleic acid and vinyl ether/maleic acid copolymers. The content of colloids is preferably between 20 and 80 wt. %, in particular between 50 and 60%. Preferably, at least 2, 5 or 10 and a maximum of 20, 50 or 80% of colloids are present.

Preferably, partly hydrolyzed or completely hydrolyzed polyvinyl alcohols having a degree of hydrolysis of from 80 to 100 mol %, in particular from 80 to 95 mol %, and a Höppler viscosity (in 4% strength aqueous solution) of from 1 to 30 mPas, preferably 3 to 15 mPas (Höppler method at 20° C., DIN 53015), are employed as colloids. Preferably, partly hydrolyzed or completely hydrolyzed, hydrophobically modified polyvinyl alcohols having a degree of hydrolysis of from 80 to 100 mol % and a Höppler viscosity in 4% strength aqueous solution of from 1 to 30 mPas, preferably 3 to 15 mPas, are also employed. Examples of these are partly hydrolyzed copolymers of vinyl acetate with hydrophobic comonomers, such as isopropenyl acetate, vinyl pivalate, vinyl ethylhexanoate, vinyl esters of saturated alpha-branched monocarboxylic acids having 5 to 11 C atoms, dialkyl maleates and dialkyl fumarates, such as diisopropyl maleate and diisopropyl fumarate, vinyl chloride, vinyl alkyl ethers, such as vinyl butyl ether, alpha-olefins having 2 to 12 C atoms, such as ethene, propene and decene. The content of hydrophobic units is preferably 0.1 to 10 wt. %, based on the total weight of the partly or completely hydrolyzed polyvinyl alcohol. Partly hydrolyzed or completely hydrolyzed copolymers of vinyl acetate with isopropenyl acetate having a degree of hydrolysis of from 95 to 100 mol % are particularly preferred. Mixtures of the polyvinyl alcohols mentioned can also be employed.

Particularly preferred polymers are those which are redispersible in water. Suitable polymers are those based on one or more monomers from the group comprising vinyl esters of unbranched or branched alkylcarboxylic acids having 1 to 15 C atoms, methacrylic acid esters and acrylic acid esters of alcohols having 1 to 15 C atoms, vinylaromatics, olefins, dienes and vinyl halides. Further suitable polymers are mentioned in WO2004/103928 on pages 8 to 10, to which reference is expressly made here.

Solids powder as claimed in one of claims 1 to 6, characterized in that it comprises at least one nonionic emulsifier having an HLB value of from 5 to 20.

The present invention also provides a process for the preparation of a solids powder, in which a core material which comprises at least one water-insoluble fatty acid salt is brought into contact with at least one anionic, cationic or nonionic emulsifier as the shell material such that a solids powder comprising particles having an average particle size of from 0.1 to 50 µm with predominantly a core-shell structure is formed, wherein the core comprises at least one water-insoluble fatty acid salt and the shell at least one anionic, cationic or nonionic emulsifier and the solids powder when introduced into water or at least one polar organic solvent or a mixture comprising water and at least one polar organic solvent, at a temperature of 23° C. while exposed to a mechanical force, forms a complete dispersion within 60 minutes or less.

In this context, the shell material is preferably brought in liquid form into contact with the core material, and, for example, the core material can be brought into contact with the shell material by mixing or spraying.

Recipe Examples 100 g of calcium stearate are added to 900 g of chalk (or other organic or inorganic carrier materials) and the entire mixture is mixed in a high-shear mixer. 20 g of emulsifier are then added to this mixture and mixed in with vigorous stirring. The product can be suspended in water with vigorous stirring.

60 g of stearic acid and 8.66 g of calcium hydroxide and 10 g of water are added to 900 g of chalk (or other organic or inorganic carrier materials) and the entire mixture is stirred in a pressure reactor at 140° C. until the direct reaction has taken place. 100 g of sodium stearate are then added to this mixture and mixed in with vigorous stirring. The product can be suspended in water with vigorous stirring.

91 g of stearic acid and 73 g of zinc acetate and 100 g of water are added to 900 g of chalk (or other organic or inorganic carrier materials) and the entire mixture is stirred in a pressure reactor at 140° C. and the water and the acetic acid are then stripped off in vacuo. 50 g of triethanolammonium stearate are added to this this mixture and mixed in with vigorous stirring. The product can be suspended in water with vigorous stirring.

100 g of sodium stearate are 45 g of zinc chloride and 100 g of water are added to 900 g of chalk (or other organic or inorganic carrier materials) and the entire mixture is stirred in a pressure reactor at 140° C. and the water is then stripped off in vacuo. 100 g of sodium stearate are then added to this mixture and mixed in with vigorous stirring. The product can be suspended in water with vigorous stirring.

200 g of sodium stearate are 45 g of zinc acetate and 100 g of water are added to 900 g of chalk (or other organic or inorganic carrier materials) and the entire mixture is stirred in a pressure reactor at 140° C. and the water is then stripped off in vacuo. The product can be suspended in water with vigorous stirring.

100 g of sodium stearate (or 10% of emulsifier) are added to 900 g of calcium stearate and the entire mixture is mixed in a high-shear mixer. The product can be suspended in water with vigorous stirring.

90 g of sodium laurate and 10 g of an emulsifier are added to 900 g of calcium stearate (or metal soaps or metal soap mixtures) and the entire mixture is mixed in a high-shear mixer. The product can be suspended in water with vigorous stirring.

50 g of emulsifier and 10 g of a low molecular weight cosurfactant (e.g. polyol) are added to 900 g of calcium stearate (or metal soaps or metal soap mixtures) and the entire mixture is mixed in a high-shear mixer. The product can be suspended in water with vigorous stirring.

10-100 g of stearic acid or zinc stearate are added to 900 g of aluminum oxide (or other organic or inorganic carrier materials) and the entire mixture is mixed in a high-shear mixer. 20 g of emulsifier are then added to this mixture and mixed in with vigorous stirring. The product can be suspended in water with vigorous stirring.

300 g of sodium oleate are added to 700 g of calcium stearate and the entire mixture is mixed in a high-shear mixer. 20 g of emulsifier are then added to this mixture and mixed in with vigorous stirring. The product can be suspended in water with vigorous stirring.

700 g of zinc stearate are melted at 130° C. and 300 g of sodium stearate are added and the entire mixture is stirred. The solidified melt is then ground and 20 g of emulsifier are added and mixed in with vigorous stirring. The product can be suspended in water with vigorous stirring.

900 g of calcium carbonate are ground with 10 g of calcium stearate and the entire mixture is then transferred into a thermomixer. An aqueous solution (emulsifier or alkali metal/ NH4 stearate) is sprayed on to this mixture and the water is evaporated with vigorous stirring. The product can be suspended in water with vigorous stirring.

90 g of sodium hydroxide, 50 g of water and 80 g of emulsifier, as well as a cosurfactant are added to 900 g of stearic acid. The entire mixture is stirred at 140° C. and the water is stripped off. 45 g of calcium acetate are added to this dried powder mixture and the mixture is mixed. The product can be suspended in hot water with vigorous stirring (dissolver disk) and the calcium stearate prepared in situ in the double reaction has a high fineness.

120 g of calcium hydroxide are added to 900 g of a triglyceride (fats, oils, vegetable, animal) and the mixture is mixed thoroughly with 100 g of water in a pressure reactor at 160° C. After cleavage of the fat the water is stripped off and an emulsifier or alkali metal/NH4 stearate is added and the mixture is processed in a mixer under high shearing forces. The product can be suspended in water with vigorous stirring.

700 g of zinc stearate are melted at 130° C. and 300 g of paraffin are added and the entire mixture is stirred under high shearing forces until the paraffin is finely dispersed. The solidified melt is then ground and 20 g of emulsifier are added and mixed in with vigorous stirring. The product can be suspended in water with vigorous stirring.

700 g of paraffin are melted at 130° C. and 300 g of sodium oleate are added and the entire mixture is stirred under high shearing forces. The solidified melt is then ground and 20 g of emulsifier are added and mixed in with vigorous stirring. The product can be suspended in water with vigorous stirring.

900 g of calcium carbonate are ground with 30 g of stearic acid and 4 g of calcium hydroxide and the entire mixture is then transferred into a thermomixer. An aqueous solution (emulsifier or alkali metal/NH4 stearate) is sprayed on to this mixture and the water is evaporated with vigorous stirring. The product can be suspended in water with vigorous stirring.

900 g of calcium stearate are mixed with 100 g of a mixture (prepared according to the following instructions: 120 g of calcium hydroxide are added to 900 g of a triglyceride and the mixture is mixed thoroughly with 100 g of water in a pressure reactor at 160° C. After cleavage of the fat the water is stripped off and sodium stearate is added and the mixture is processed in a mixer under high shearing forces) and propanetriol.

The product can be suspended in water with vigorous stirring.

50 g of calcium hydroxide and 40 g of sodium hydroxide are added to 900 g of a triglyceride (fats, oils, vegetable, animal) and the mixture is mixed thoroughly with 100 g of water in a pressure reactor at 160° C. After cleavage of the fat the water is stripped off and an emulsifier is added and the mixture is processed in a mixer under high shearing forces. The product can be suspended in water with vigorous stirring.

700 g of a hardened fat and 100 g of a highly absorbent material (montmorillonite, bentonite, bleaching earth, zeolite etc.) are melted at 130° C. and 100 g of sodium oleate are added and the entire mixture is stirred under high shearing forces. The solidified melt is then ground and 20 g of emulsifier are added and mixed in with vigorous stirring. The product can be suspended in water with vigorous stirring.

700 g of a paraffin and 100 g of a highly absorbent material (montmorillonite, bentonite, bleaching earth, zeolite etc.) are melted at 130° C. and 100 g of sodium oleate are added and the entire mixture is stirred under high shearing forces. The solidified melt is then ground and 20 g of emulsifier are added and mixed in with vigorous stirring. The product can be suspended in water with vigorous stirring.

50 g of zinc stearate are added to 900 g of microcellulose <10 μm and the entire mixture is mixed in a thermomixer at 130° C. 50 g of sodium stearate are then added to this mixture and mixed in with vigorous stirring. The product can be suspended in water with vigorous stirring.

The invention claimed is:

1. A solids powder comprising particles having an average particle size of from 0.1 to 50 μm with predominantly a core-shell structure, wherein the core is made of a core material which comprises at least one water-insoluble fatty acid salt and the shell is made of a shell material which comprises at least one anionic, cationic or nonionic emulsifier, or mixtures thereof, and the solids powder when introduced into water, at least one polar organic solvent, or a mixture comprising water and at least one polar organic solvent, at a temperature of 23° C. while exposed to a mechanical force, forms a complete dispersion within 60 minutes or less.

2. A solids powder as claimed in claim 1, wherein the core comprises a fatty acid salt with a metal cation or an ammonium cation, a mixture of fatty acid salts of at least two different metal cations or at least two different ammonium cations, or a mixture of at least one metal cation and at least one ammonium cation, wherein the metal cations are selected from the group consisting of alkali metals, alkaline earth metals, zinc, aluminum and rare earths.

3. A solids powder as claimed in claim 1, wherein the core material comprises at least one organic or inorganic carrier material.

4. A solids powder as claimed in claim 1, wherein the content of fatty acid salts of fatty acids having 8 to 18 C atoms, based on the total amount of the fatty acid salts in the shell material, makes up 20 wt. % or more than 20 wt. %.

5. A solids powder as claimed in claim 1, comprising at least one fatty acid salt of one or more of the metals sodium, potassium, zinc, magnesium and calcium.

6. A solids powder as claimed in claim 1, wherein the shell comprises an anionic emulsifier, a nonionic emulsifier, or mixtures thereof.

7. A solids powder as claimed in claim 1, comprising at least one additive selected from solvents, binders, polymers, colloids, surfactants, emulsifiers or solvents, or a mixture of two or more thereof.

8. A solids powder as claimed in claim 1, comprising at least one nonionic emulsifier having an HLB value of from 5 to 20.

9. A process for the preparation of a solids powder, comprising bringing a core material which comprises at least one water-insoluble fatty acid salt into contact with at least one anionic, cationic or nonionic emulsifier, or a mixture thereof, as the shell material such that a solids powder comprising particles having an average particle size of from 0.1 to 50 μm with predominantly a core-shell structure is formed, wherein the solids powder, when introduced into water, at least one polar organic solvent, or a mixture comprising water and at least one polar organic solvent, at a temperature of 23° C. while exposed to a mechanical force, forms a complete dispersion within 60 minutes or less.

10. The process as claimed in claim 9, wherein the shell material is brought in liquid form into contact with the core material.

11. The process as claimed in claim 9, wherein the core material is brought into contact with the shell material by mixing.

12. The process as claimed in claim 9, wherein the core material is brought into contact with the shell material by spraying.

* * * * *